United States Patent
Bolton (12) 
(10) Patent No.: US 6,696,092 B2
(45) Date of Patent: *Feb. 24, 2004

(54) ENDOTHELIAL LINING EFFECTS AND TREATMENT OF VASOSPASTIC DISORDERS

(75) Inventor: Anthony E. Bolton, Tideswell (GB)

(73) Assignee: Vasogen Ireland Limited, Shannon (IE)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

This patent is subject to a terminal disclaimer.

(21) Appl. No.: 09/267,773

(22) Filed: Mar. 15, 1999

(65) Prior Publication Data

US 2002/0168420 A1 Nov. 14, 2002

Related U.S. Application Data (60) Continuation-in-part of application No. 08/477,818, filed on Jun. 7, 1995, now Pat. No. 5,834,030, which is a continuation-in-part of application No. 07/941,326, filed on Sep. 4, 1992, now abandoned, which is a continuation-in-part of application No. 07/832,798, filed on Feb. 7, 1992, now abandoned, which is a division of application No. 08/765,225, filed as application No. PCT/CA96/00282 on May 3, 1996, now abandoned.

(30) Foreign Application Priority Data

May 5, 1995 (GB) ............................................. 9509197
Nov. 2, 1995 (GB) ............................................. 9522475

(51) Int. Cl.$^7$ ......................... A61K 33/00; A61K 35/14; A61K 41/00; A61L 2/10
(52) U.S. Cl. ..................... 424/613; 250/493.1; 424/529; 424/534; 435/2; 604/4.01
(58) Field of Search ......................... 250/493.1; 422/24, 422/44, 45, 46; 424/613, 810, 529, 534; 514/929; 534/2; 604/4, 4.01; 435/2

(56) References Cited

U.S. PATENT DOCUMENTS

| 695,657 A | 3/1902 | Smith .......................... 604/25 |
| 3,715,430 A | 2/1973 | Ryan .......................... 424/613 |
| 4,632,980 A | 12/1986 | Zee et al. .................... 530/380 |
| 4,831,268 A | 5/1989 | Fisch et al. ............. 250/432 R |
| 4,968,483 A | * 11/1990 | Muller et al. ................. 422/45 |
| 4,983,637 A | 1/1991 | Herman ...................... 514/724 |
| 5,052,382 A | 10/1991 | Wainwright |
| 5,100,378 A | 3/1992 | Morgan, Jr. |
| 5,547,635 A | 8/1996 | Duthie, Jr. .................... 422/24 |
| 5,591,457 A | * 1/1997 | Bolton ........................ 424/613 |
| 5,834,030 A | * 11/1998 | Bolton ........................ 424/613 |

FOREIGN PATENT DOCUMENTS

| EP | 582739 | 2/1994 |
| EP | 624770 | 11/1994 |
| WO | 93/15779 | 8/1993 |
| WO | 95/20649 | 8/1995 |
| WO | 93/15778 | 8/1998 |

OTHER PUBLICATIONS

Harrison's Principles of Internal Medicine (1994, 13th Ed.), pp. 66–70, 1135–43.*
Harrison's Principles of Internal Medicine (1983, 10th Ed.), pp. 1491–1498.*
Miller et al.,'Is variant angina the coronary manisfestation of a generalized vasospastic disorder?' (1981), New England Journal of Medicine, vol. 304, No. 13, pp. 763–766.*
Drug Fact's and Comparisons (2000, 54th Ed.), pp. 458–466, 849–61.*
Ozon–Omed, "helping the body heal itself," Mueller Medical International Inc. (1990).
Abstract No. 1989:121366, "Preparation of oxidized blood fractions . . . " (1989).
Abstract No. 1995:283376, "Method for introducing oxygen into blood . . . " (1995).
Abstract No. 1998031574, "Effect of combined heat, ozonation and ultraviolet . . . " (1998).
Synder et al, "Biological Roles of Nitric Oxide," Scientific American, May 1992, pp. 68–77.
Bredt et al, "Cloned and expressed nitric oxide synthase . . . " Nature, vol. 351, pp. 714–718(1991).
"Secondary prevention of cascular disease by . . . " British Medical Journal, vol. 296, pp. 320–331 (1988).
German 1 068 428, Jentjens et al, Verfahren und Einrichtung zur Herstellung von oxygeniertem Blut (1960).
Goldman et al, Abstract of "Serum Soluble Interleukin 2 Receptor Levels in Erythtodermic . . . ," (1993).

* cited by examiner

Primary Examiner—Thurman K. Page
Assistant Examiner—Frank Choi
(74) Attorney, Agent, or Firm—Swiss Law Group (57) ABSTRACT

Vasospastic disorders are treated by administering to the patient an aliquot of autologous blood which has been subjected simultaneously to heat, ultraviolet irradiation and oxidative environment so as to render the blood aliquot capable of generating in the patient's blood stream after administration a population of stimulated leukocytes having upregulated expression of CD25 cell surface markers, along with an enhancement of endothelial function in the patient.

13 Claims, 2 Drawing Sheets

ENDOTHELIAL LINING EFFECTS AND TREATMENT OF VASOSPASTIC DISORDERS

This Application is a continuation-in-part of U.S. application Ser. No. 08/477,818 filed Jun. 7, 1995 and issued Nov. 10, 1998 as U.S. Pat. No. 5,834,030, which is in turn a continuation-in-part of U.S. application Ser. No. 07/941,326 filed Sep. 4, 1992 (abandoned), which was a continuation-in-part of U.S. application Ser. No. 07/832,798 filed Feb. 7, 1992 (abandoned). It is also a division of U.S. application Ser. No. 08/765,225, filed Apr. 11, 1997 (abandoned), which is a §371 application of PCT/CA96/00282, filed May 3, 1996. The PCT application claims priority to Great Britain Patent Application Serial No. 9509197.1, filed May 5, 1995 and Great Britain Patent Application Serial No. 9522475.4, filed Nov. 2, 1995.

FIELD OF THE INVENTION

This invention relates to treatment of blood cells, and the use of treated, modified blood cells in connection with certain abnormal mammalian physical conditions and disease states. More specifically, it relates to modified mammalian blood and blood cells, methods of achieving the modified mammalian blood and blood cells, and the treatment, among other disorders, of vascular disorders associated with deficient endothelial function, such as vasospatic disorders, in a mammalian patient by administration to the patient of such modified blood and blood cells.

BACKGROUND OF THE INVENTION

The control and regulation of blood flow through the cardiovascular system of a mammal is well recognized to be of importance in connection with cardiovascular disorders such as atherosclerosis, peripheral vascular disease and many other circulatory disorders. There is an emerging body of literature which indicates that the endothelium plays a major role in the regulation of blood flow through the cardiovascular system. The endothelium is a cellular structure which lines the blood vessels, communicating with the smooth muscle layer of the blood vessel walls. Contraction of this muscle layer causes the blood vessels to constrict (vasoconstriction), and relaxation of this muscle layer causes the blood vessels to expand (vasodilation). A normally functioning endothelium effectively controls the smooth muscles of the vessel wall, by secreting vasodilators or vasoconstrictors which diffuse or are carried to the muscle fibres to cause the muscle fibres either to relax or to contract. One such vasodilator secreted by the endothelium is commonly referred to as "endothelium derived relaxing factor" (EDRF), but has recently been established to be nitric oxide, a form thereof or a closely related compound. In addition to regulating blood flow, nitric oxide is recognized as having many other actions within the body, including neurotransmis-sion, a smooth muscle controlling function within the gastrointestinal tract, both natural and drug induced analgesia, a role in impotence and in tumour toxicity.

It is believed that defective functioning of the endothelium of a patient is an underlying factor in many cardiovascular diseases observed in mammalian patients. For example, a patient with atherosclerosis has excessive quantities of lipid underlying the endothelium, including oxidized low density lipoprotein (containing cholesterol) which is believed to interfere with the proper functioning of the endothelial cells.

SUMMARY OF THE INVENTION

The present invention is based upon the discovery that one can extracorporeally subject an aliquot of a mammalian patient's blood, or the separated cellular fractions of the blood, or mixtures of the separated cells, including platelets, to certain stressors and create in the aliquot modified leukocytes. On re-introduction of the aliquot to the patient's body by various routes including intra-muscular injection, the modified leukocytes have certain beneficial effects. One of these effects is stimulation of the activity of a functionally deficient endothelium.

The modified leukocytes of the present invention can be obtained by subjecting the aliquot of the patient's blood, or the separated cellular fractions of the blood, or mixtures of the separated cells, including platelets, to stressors selected from heat, ultraviolet radiation and oxidative environments such as treatment with ozone/oxygen mixtures, or any combination of such stressors, simultaneously or sequentially.

Thus, according to the present invention, ex vivo treatment of the blood, or the separated cellular fractions of the blood, or mixtures of the separated cells, including platelets, promotes the subsequent development of modified leukocytes, which are different from the untreated cells that are found in the peripheral blood of normal individuals and patients before receiving this treatment, in that they cause an n vivo effect.

The effects of the modified leukocytes of the present invention, when re-injected into the mammalian patient's body, are several in number. Firstly, there is an effect on other leukocytes or their progenitors which have not been modified by the externally applied stressors, as a result of cell-to-cell communication, a widely recognised phenomenon among cells of the immune system. The result of injecting the blood subjected to stressors outside the body is the upregulation of specific cell surface markers such as HLA-DR and CD25 on other, non-treated leukocytes in the peripheral blood, circulating in the patient. This is indicative of an enhanced immune system. It appears that the treated leukocytes release cytokines (intercellular messenger peptides and proteins), or stimulate leukocytes of the recipient to do so, initiating a cascade phenomenon which affects a number of the quiescent leukocytes in the peripheral blood and causes them to become stimulated. This apparently leads to improved blood flow at sites in the body far removed from the site of injection of the treated leukocytes.

Secondly, the stimulated leukocytes present in the blood circulation, perhaps through the intermediary of the same or similar cytokines and probably aster physical contact or binding to the endothelium via cell adhesion molecules, act upon the endothelium, either directly or indirectly, to increase the endothelial vasodilator function probably by increasing the production and/or action of vasodilators such as nitric oxide, prostacyclin and/or by inhibiting the production and/or action of vasoconstrictors, so as to increase blood flow. This can be manifested either as a restoration of the function of a portion of the endothelium which has become defective, the portion being close to or remote from the site of injection. Such restoration of function may occur through repair of deficient cells or an enhanced rate of replacement of damaged cells. It can also be manifested as an overall improvement in endothelial function. This increased blood flow resulting from increased endothelial vasodilator function, and the consequent increase in oxygenation of tissues, is indicative of use of the process of the present invention in treatment of patients with vascular disease including those with advanced peripheral vascular disease, those with chronic varicose ulcers, and those at risk of developing gangrene which frequently results in amputation. In general, the leukocytes according to the present invention are indicated for use in treating any type of vascular disease either involving partial or complete blood vessel occlusion leading to restricted blood flow or dysfunction of the mechanisms required to permit adequate vasodilation such that tissues including those of the central nervous system, heart, lungs, gastrointestinal tract, liver, kidneys, placenta or extremities would be acutely or chronically affected in terms of structure or function.

DESCRIPTION OF THE PREFERRED EMBODIMENTS

Figure 1:
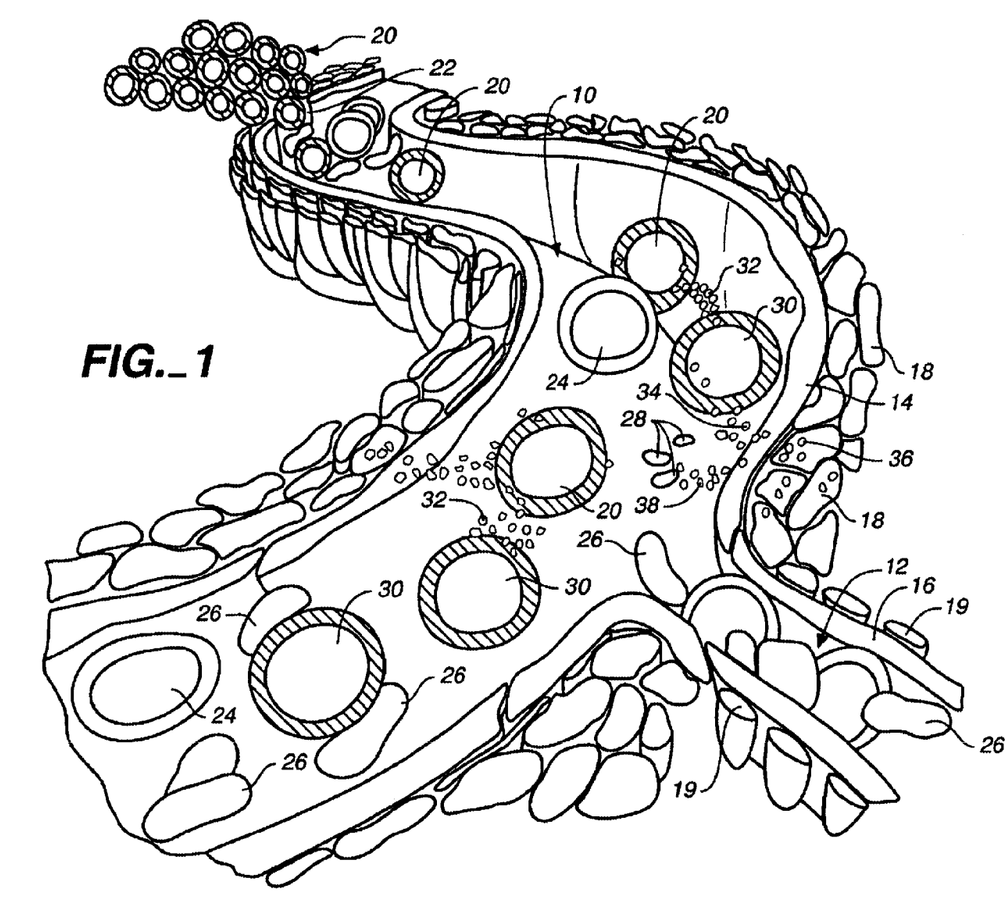
FIG. 1 is a diagrammatic illustration of the believed mode of action of the injected leukocytes according to the present invention, in the vascular system.

With reference to the FIG. 1, there is diagrammatically illustrated an arteriole 10. An arteriole is a blood vessel forming part of the mammalian vascular system, of a size smaller than an artery, and which receives circulating blood from an artery, fed from the heart. Arterioles gradually decrease in size, in the downstream direction. A metarteriole 12, which is a smaller terminal branch of the arteriole 10, is shown branching off the arteriole 10. Metarterioles such as 12 lead to capillaries which are the site of nutrient and gaseous exchange between the blood and the tissues, with oxygen diffusing from the blood to the tissues and carbon dioxide diffusing from the tissues to the blood. The arteriole 10 is lined with a cellular layer of endothelium 14. Surrounding the exterior of the arteriolar endothelium 14 is a layer of smooth muscle 18, which can contract or expand to cause alterations in the size of the arteriole 10, causing either vasodilation to increase the amount of blood flow therethrough or vasoconstriction to reduce the amount of blood flow therethrough. The metarteriole 12 is similarly lined with endothelium 16 and has a single layer of smooth muscle 19, functioning similarly.

As in the case of all the other blood vessels in the body, of all the various sizes, capillaries are lined with endothelium. However, there is no smooth muscle layer associated with the capillaries.

According to the preferred process of the present invention, an aliquot of blood, or the separated cellular fractions of the blood, or mixtures of the separated cells, including platelets, is extracted from the patient and treated with certain stressors, described in more detail below. The effect of the stressors is to modify leukocytes in the aliquot. These modified leukocytes 20, along with the rest of the aliquot, are re-injected intramuscularly and, after a period within the muscle, of uncertain and probably variable duration, they probably gain entry to the general circulation by passing through the blood vessel wall, where mixing with the blood occurs. Downstream from the point of entry 22, therefore, the blood will contain modified leukocytes 20 in addition to unmodified leukocytes 24, red blood cells 26 and platelets 28, as well as other components.

The injection of modified leukocytes 20 appears to have a number of unexpected effects on the arteriole 10 and on the blood flowing through it. One effect is the stimulation of quiescent leukocytes 24, which have not been subjected to the stressors outside the body, to transform into stimulated leukocytes 30. This activation process may occur in sites other than the blood vessels, for example in immune system organs such as lymph nodes, spleen or bone marrow, and may involve leukocyte progenitors in addition to or alternatively to mature leukocytes. Thus a cascade mechanism is set in motion. This is believed to be effected by the secretion of certain cytokines 32, the precise nature of which is uncertain, either from the modified leukocytes 20 themselves or by the stimulation of endogenous leukocytes 30 by direct cell—cell interaction. These mechanisms serve to effect stimulation of previously quiescent leukocytes or progenitors to create the stimulated leukocytes 30. The stimulated leukocytes 30 probably adhere to the damaged endothelial cells via cell adhesion molecules such as ICAM-1 expressed on the endothelial cells interacting with activated LPA-1 expressed on certain activated leukocytes. Other cytokines 34, perhaps originating from these adherent leukocytes and which may in fact be the same as or different from the cytokines 32, contact the endothelium 14, and cause it to secrete vasodilators 36 which have the effect of relaxing the smooth muscle 18 to cause a degree of vasodilation. Other secretions 38 released from the endothelium 14 by the cytokines 34, which may or may not be the same substances or mixture of substances as the vasodilators 36, contact the platelets 28, and have the effect of inhibiting their ability to aggregate. Whilst the accompanying figure diagrammatically illustrates endothelial effects at the endothelium of an arteriole of the vascular system, it appears that the process of the invention has a similar effect on endothelial cells at all levels of the vascular tree.

It is believed that one of the components of the vasodilators 36, and one of the components of the secretions 38, is endothelium derived relaxing factor EDRF, probably nitric oxide or closely related substances, and a second component is prostacyclin. Alternative or additional sources of nitric oxide and/or other vasodilators resulting from a treatment according to the present invention may be stimulated leukocytes present in the circulation or stimulated platelets present in the circulation.

The stressors to which the leukocytes are subjected ex vivo according to the invention are selected from temperature stress (blood temperatures above or below body temperature), an oxidative environment and ultraviolet radiation, individually or in any combination, simultaneously or successively. The leukocytes are subjected to the stressors as a part of an aliquot of mammalian blood or the separated cellular fractions of the blood, or mixtures of the separated cells, including platelets, extracted from the patient to whom the aliquot is to be injected following subjection to the stressors. Suitably the aliquot has a volume of from about 0.1–100 mls, preferably 5–15 mls, a most preferred, typical aliquot being 10 mls in volume.

It is preferred, according to the invention, to apply all three of the aforementioned stressors simultaneously to the aliquot under treatment, in order to ensure the appropriate modification of a sufficient number of leukocytes. Care must be taken not to utilised an excessive level of the stressors, to the extent that the cells or any parts of them become irreparably damaged, or that the cell membrane is caused to be disrupted.

The temperature stressor, when it is applied, must keep the aliquot liquid, and should not heat it above about 55° C., for fear of damaging the cells. Preferably the temperature stressor warms the aliquot being treated to a temperature above normal body temperature, i.e., to about 37–55° C., and most preferably from about 40–50° C.

The oxidative environment stressor can be the application to the aliquot of liquid or gaseous oxidizing agents. Preferably it involves exposing the aliquot to a mixture of medical grade oxygen and ozone gas, most preferably by bubbling through the aliquot, at the aforementioned temperature range, a stream of medical grade oxygen gas having ozone as a minor component therein. Suitably the gas stream has an ozone content of-from about 1.0–100 μg/ml, preferably 3–70 μg/ml, and most preferably about 5–50 μg/ml. The gas stream is supplied to the aliquot at a rate of from about 0.01–2.0 liters/minute, preferably at about 0.05–5.0 liters per minute and most preferably at about 0.06 liters per minute (STP).

The ultraviolet radiation stressor is suitably applied by irradiating the aliquot under treatment from an appropriate source of UV radiation while the aliquot is maintained at the aforementioned temperature and while the oxygen/ozone gaseous mixture is being bubbled through the aliquot. Appropriate UV sources are UV lamps emitting in the C-band wavelengths, i.e. at wavelengths shorter than about 280 nm. Ultraviolet radiation corresponding to standard UV-A and UV-B sources can also be used. Emissions at wavelength 253.7 nm are particularly suitable. An appropriate dosage of such UV radiation, applied simultaneously with the aforementioned temperature and oxidative environment stressors, is obtained from lamps with a power output of from about 15 to about 25 watts, at the chosen UV wavelength, arranged to surround the sample container holding the aliquot, each lamp providing an intensity, at a distance of 1 meter, of from about 45–65 mW/sq.cm. Up to eight such lamps surrounding the sample bottle, with a combined output at 253.7 nm of 15–25 watts, operated at an intensity to deliver a total UV light energy at the surface of the blood of about 0.025–10, preferably about 0.1–0.5 joules/cm$^2$, may advantageously be used. Such a treatment provides an aliquot which contains stimulated leukocytes according to the invention in appropriate amounts to cause the effects outlined above ready for re-injection into the patient.

The time for which the aliquot is subjected to the stressors is normally within the time range of from about 0.5–60 minutes. This depends to some extent upon the chosen intensity of the UV irradiation, the temperature and the concentration of and rate at which the oxidizing agent is supplied to the aliquot. The more severe the stressors applied to the aliquot, generally the shorter time for which they need to be applied. Some experimentation to establish optimum times may be necessary on the part of the operator, once the other stressor levels have been set. Under most stressor conditions, preferred times will be in the approximate range 2–5 minutes, and normally around 3 minutes. The starting blood temperature, and the rate at which it can be warmed or cooled to a predetermined temperature, tends to vary from patient to patient.

In the practice of the preferred process of the present invention, the blood aliquot (or the separated cellular fractions of the blood, or mixtures of the separated cells, including platelets, these various leukocyte-containing combinations, along with whole blood, being referred to collectively throughout as the "aliquot") may be treated with the stressors using an apparatus of the type described in U.S. Pat. No. 4,968,483 Mueller. The aliquot is placed in a suitable, sterile, radiation-transmissive container, which is then fitted into the machine. The temperature of the aliquot is adjusted to the predetermined value, e.g. 42.5° C., and the UV lamps are switched on for a fixed period before the gas flow is applied to the aliquot providing the oxidative stress, to allow the output of the UV lamps to stabilize. Then the oxygen/ozone gas mixture, of known composition and controlled flow rate, is applied to the aliquot, for the predetermined duration of 0.5–60 minutes, preferably 2–5 minutes and most preferably about 3 minutes as discussed above, so that the aliquot experiences all three stressors simultaneously. In this way, appropriately modifieded leukocytes according to the present invention are generated in numbers sufficient to achieve the desired effects.

Another characteristic of the modified leukocytes of the present invention is their ability to generate in the bloodstream of the patient, after re-injection, stimulated leukocyes having an increase in activation markers, for example CD 25 (IL-2 receptor), Ber-Mac 3 and HLA-DR (T-cell and monocyte activation). These cell surface markers are surface proteins, the quantities of which are increased by injecting the modified leukocytes prepared using the stressors of the preferred process of the present invention i.e. temperature, an oxidising environment, and UV radiation. They can be quantified by staining techniques and use of conventional monoclonal antibody techniques.

The proper functioning, or lack thereof, of the endothelium of a patient, at a particular location, can be tested by using a method which involves the iontophoretic introduction of acetylcholine through the skin, and measurement of its effect on superficial blood at the chosen location.

Acetylcholine added to a blood vessel which has intact, properly functioning endothelium, stimulates the production and secretion of nitric oxide by the endothelium. The nitric oxide so produced acts as a vasodilator and causes the smooth muscle cells to relax. The effect of such vasodilation can be quantitated by measuring the flow of blood in the vessel, e.g. by laser Doppler flowmetry. If, however, the endothelium of the patient has a major functional defect, the acetylcholine may act directly on the smooth muscles themselves, and cause them to contract, resulting in vasoconstriction, the opposite of the effect observed when the patient's endothelium is functioning normally.

Endothelial function may accordingly be examined clinically as follows. Acetylcholine is applied to the skin of the patient and a small electric current is applied across the skin between two adjacent electrodes, one positively and one negatively charged (iontophoresis). Acetylcholine, being a charged molecule, passes through the skin with the current to the superficial blood vessels immediately below the skin surface. At this site, acetylcholine acts on the endothelial cells of the blood vessels, stimulating them to produce EDRF (e.g. nitric oxide), resulting in vasodilation (endothelial dependent vasodilation) and an increase in blood flow, which is measured by laser Doppler flowmetry, for example. This technique is known, in general terms— see, for example, Chowienczyk et.al., "Impaired endothelium-dependent vasodilation of forearm resistance vessels in hypercholesterolaemia", *The Lancet*, Vol. 340, Dec. 12, 1992, p.1430.

A specific preferred application for the present invention is in treatment for, or at least alleviation of the symptoms of, the vasospastic type diseases as exemplified by Raynaud's Phenomenon and other vasospastic disorders such as migraine, cluster headache and syndrome X. Raynaud's Phenomenon is a state in which the fingers and/or toes undergo a series of colour changes, white (vasospasm)$_1$ then blue (capillary stagnation) then red (arterial dilation), lasting a variable time and for a variable frequency, and with or without pain. Raynaud's Disease or primary Raynaud's is the term for Raynaud's Phenomenon in the absence of any other detectable disease. Raynaud's syndrome, or secondary Raynaud's, is the term for Raynaud's Phenomenon associated with other diseases.

Whilst Raynaud's is not in itself life threatening, it may lead to the onset of other pathological conditions, and to-date there has been no effective cure put into general practice for it. A patient suffering from Raynaud's must simply endure the associated pain and discomfort. In a small proportion of cases, the ischemia of the digits resulting from extreme vasospasm may lead to skin ulceration and gangrene, which may result in amputation. Raynaud's Phenomenon can affect patients at substantially any age, and affects about four times as many women as men.

Following one or more treatments according to the procedure of the invention, spaced at appropriate intervals, dramatic alleviation of the symptoms of the Raynaud's phenomenon is experienced, in the cases of all of the patients on which the treatment has so far been employed. Iontophoretic measurements conducted on the blood flow of the subject patients, before and after undergoing the treatment according to the invention, have shown an enhancement of the endothelial performance in the patients of concern, and an alleviation of the Raynaud's phenomenon symptoms.

Thus from another aspect, the present invention provides an aliquot of autologous human blood for administration to a patient to alleviate Raynaud's phenomenon in the patient, the aliquot of autologous blood having been subjected, in vitro, to at least one stressor selected from heat, UV radiation and ozone/oxygen mixture to stimulate leucocytes therein, to the extent that, upon re-injection into the patient, a significant enhancement of endothelial function to cause vasodilation is experienced.

The invention is further illustrated and described with reference to the following specific examples.

EXAMPLE 1

A patient suffering from primary Raynaud's disease was given a course of treatment under carefully controlled clinical conditions, according to the present invention. Each treatment administered to the patient involved removing a small aliquot of the patient's blood, exposing it to stressors ex vivo and re-introducing the treated blood aliquot to the patient as described in the invention. The course of treatment administered to the patient comprised ten such individual treatments, one administered each day over a period of about two weeks. Raynaud's disease is a disorder associated with peripheral vasospasm and inadequate blood flow at the extremities of the patient's body, such as the fingers, characterized initially by marked pallor of the fingers on exposure to cold, often followed by a subsequent phase of cyanosis (bluish colour) and a slowing of the restoration of blood flow after cold exposure ceases.

The subject of this experiment was a female patient of about 24 years of age who had suffered from primary Raynaud's disease for at least 10 years, with the fingers of both hands being severely affected. Prior to commencing the course of treatments according to the invention, the blood flow in the superficial blood vessels of the fingers was measured by laser Doppler flowmetry and photoplethysmography in response to mild cold and warm stresses of the hand. The skin surface temperatures of the fingers were also measured by a thermographic technique in response to warm and cold stress of the hands. The blood flow in response to iontophoretic introduction of acetyl choline was measured by laser Doppler flowmetry, prior to commencing the course of treatments.

10 mls of the patient's blood were extracted from an arm vein, anticoagulated and collected in a sterile sample bottle. This sample was subjected to heat—UV radiation— oxidising (oxygen/ozone mixture) stressors according to the procedure of the invention, in an apparatus generally as illustrated in aforementioned U.S. Pat. No. 4,968,483 Mueller. The blood sample was heated to 42.5° C. and UV irradiation of wavelength 253.7 was applied to it. Upon reaching the required temperature (42.5° C.), a gaseous mixture of medical grade oxygen with an ozone content of 12.5 micrograms per ml, at a gas flow rate of about 60 ml/min was bubbled through the sample for 3 min.

After the ex vivo treatment of the blood sample had been completed according to the procedure of the invention, the sample was re-injected into the gluteal muscle of the patient. Shortly after completion of the course of ten treatments over a period of two weeks, the patient reported an alleviation of her symptoms of Raynaud's disease. This state of improvement persisted for at least two months after the completion of the course of treatment.

The skin temperature and the blood flow measurements in response to warm and cold stress and the blood flow after iontophoretic introduction of acetyl choline were repeated after the course of treatment according to the invention. The responses to warm and cold stress were reflective of a more normal response after treatment than before. The blood flow response to acetyl choline after treatment was increased, indicating an increase in the ability of the endothelium to produce vasodilators following the treatment. All the measurements showed evidence of an increase in peripheral blood flow following the treatment along with the alleviation of the symptoms of Raynaud's disease.

Generation in the blood of treated patients of increased levels of prostacyclin is also an effect resulting from the ex vivo stressing of the blood cells in the manner described, according to the present invention. Amelioration of the effects of a defective endothelium with its consequent alleviation of abnormal conditions associated therewith, such as vasospastic disorders as exemplified by Raynaud's disease, is just one of the several beneficial effects likely to be derived by correct medical use of the processes, techniques and modified leukocytes forming aspects of the present invention.

EXAMPLE 2

Four patients, including the subject of Example 1, human females ranging in age from 15 to 84 years, and all suffering from primary Raynaud's phenomenon, were subjected to a course of treatment according to the present invention. Treatment was given by skilled, qualified personnel, in a medical hospital facility on an out-patient basis.

Each treatment administered to a patient involved removing a 10 ml aliquot of the patient's blood, into an apparatus as generally illustrated in aforementioned U.S. Pat. No. 4,968,483 Mueller, heating the sample to 42.5° C. and exposing it to UV irradiation at wavelength 253.7 nm. Upon reaching the required temperature (42.5° C.), a gaseous mixture of medical grade oxygen with an ozone content of 12.5 micrograms per ml, at a gas flow rate of about 60 ml/min was bubbled through the sample for 3 minutes.

After the ex viva treatment of the blood sample had been completed in this manner, the sample was re-injected into the respective patient via the gluteal muscle. Each patient underwent a course of 10 such treatments over a period of 2–4 weeks, the individual treatments being spaced apart by about 1–3 days.

Subjectively, every patient reported a very significant alleviation of her Raynaud's symptoms, after completion of the course of treatments. This state of improvement persisted for at least two months after the completion of the course of treatment. In the case of the 14 year old female patient, she exhibited as part of the Raynaud's symptoms initially, small, slow healing ulcerations of the feet, around the toes. All of these had healed by the end of the course of 10 treatments. The 84 year old patient initially had noticeably disfigured fingernails at the fingernail beds, resulting from reduced nutrition and reduced oxygenation caused by lack of circulation of blood thereto. At the end of the course of treatment, new growth of nails from the nail bed had started and was clearly visible.

EXAMPLE 3

In the case of each patient, objective measurements of blood flow, before and after the course of treatments, were made by the iontophoretic technique using acetylcholine previously described. The iontophoretic applications and measurements were made on the patients' forearms. The initial measurements on each patient were taken immediately before the first treatment (i.e. during visit 1). The subsequent measurements were all taken one day after the completion of the course of ten treatments (i.e. during visit 11) and again on a follow-up basis two or three weeks later (i.e. during visit 12). One of the four patients was given a second, subsequent course of five further treatments. Blood flow was measured by laser Doppler flowmetry, to give an indication of vasodilation.

For each measurement, a reservoir containing acetylcholine was mounted on the patient's arm with the acetylcholine in contact with the patient's skin. Electrodes were inserted into the reservoir, so that a current of known but variable magnitude could be applied to the reservoir to exert an iontophoretic effect. The done of acetylcholine applied to the skin is a function of the time of acetylcholine-skin contact and the voltage applied between the electrodes, thereby giving a dose in arbitrary units.

Figure 2:
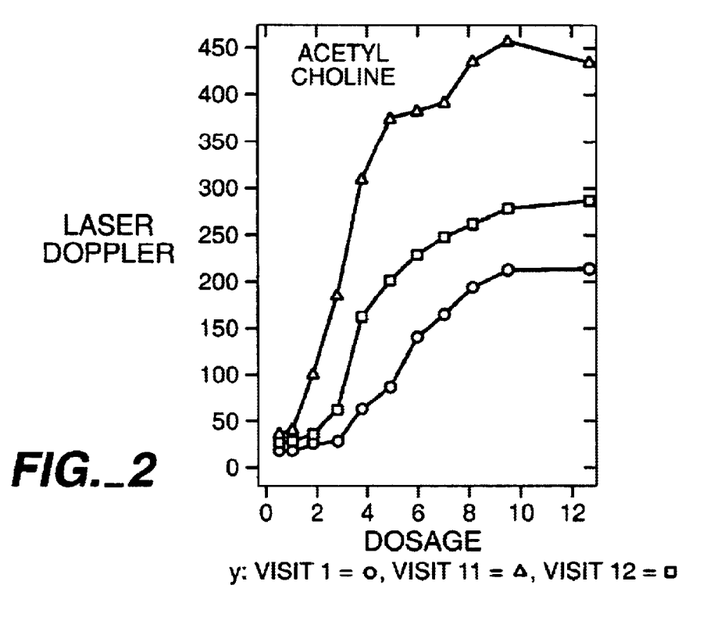
FIGS. 2 and 3 are graphical presentations of the results of clinical tests of the use of the present as described in Example 3 below.

FIG. 2 of the accompanying drawings presents a graph of observed laser Doppler flow of blood, against dosage in arbitrary units determined as above, for one representative patient. The duration of the iontophoresis was arbitrarily divided into various equal time intervals or epochs. The mean flow at each epoch is plotted against time, with the mean plotted at the mid time point of each epoch. The curve denoted by circles is that obtained from testing conducted before the first treatment, i.e. on the patient's first visit. As shown, blood flow increases in a generally sigmoidal fashion as the acetyl choline dosage (function of contact time and applied iontophoretic voltage) increases. The curve denoted by triangles is that obtained in a similar manner, on the patient's 11th visit, one day after the conclusion of the course of ten treatments. The curve denoted by squares is that obtained on the patient's 12th visit, twenty eight days after the 11th visit. Effectively, these are dose response curves. A significant increase in blood flow in response to acetyl-choline, indicative of an enhanced endothelial function, after the course of treatment, is evident from these curves.

The shapes of the respective curves indicate that increasing doses of acetylcholine cause increasing levels of blood flow, up to a plateau level in each case. This is explained by the fact that the acetylcholine is stimulating the production and secretion of the vasodilator nitric oxide (EDRF) by the endothelium, and that the endothelium is acting normally.

Figure 3:
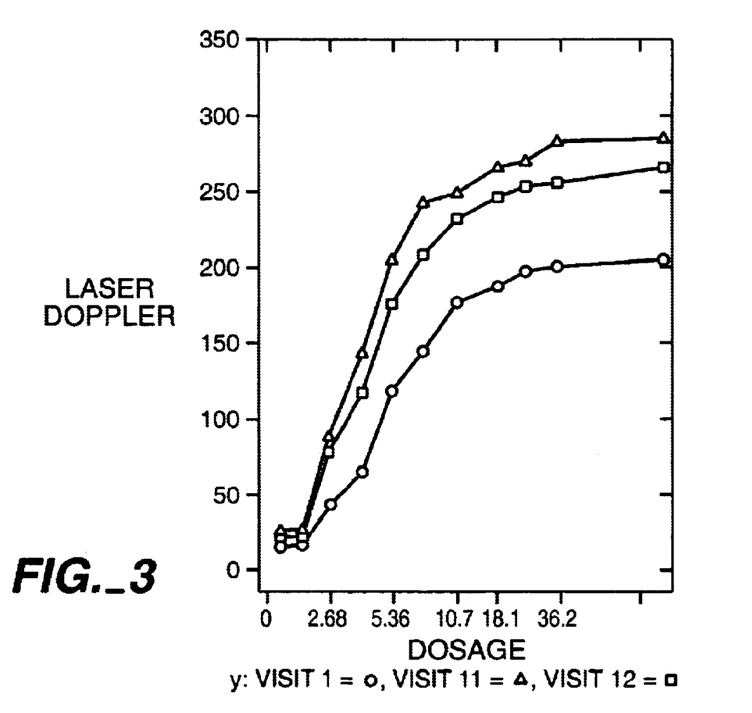

All four of the patients treated showed essentially similar results, those presented on FIG. 2 being representative, and from a single patient. FIG. 3 of the accompanying drawings shows similar curves to FIG. 2, but derived from the means of the measured blood flows of all four of the patients. As in the case of the FIG. 2 curves from the one patient, the curves denoted by circles are the mean blood flow values, at various, increasing doses of acetylcholine from the four patients before the first treatment. The curves denoted by triangles are mean values from one day after the conclusion of the course of treatments. The curves denoted by squares are mean values from twenty eight days after the conclusion of the course of treatments. The dosage response trend is clearly apparent from the curves presented as FIG. 3.

EXAMPLE 4

The iontophoresis data obtained from all four patients as described above, was subjected to statistical analysis, using the data of each of the four patients obtained before any treatment, and the data obtained from all four patients two to three to four weeks after completion of the course of 10 treatments (visit 12).

As noted above, in obtaining the curves shown on FIG. 2, the mean flow at each epoch is plotted against time, with the mean plotted at the mid time point of each epoch. Since the graphs indicate that the flow increased in a sigmoid fashion, the slope of the increase was calculated, in each case, using the mean flows from the epoch with a curve starting to rise, to the point where the curve started to become asymptotic. The regression analyses used to calculate these slopes all accounted for greater than 85% of the variation, and were therefore considered a very good fit. There was also calculated a total area under the curve (AUC) from the point where the curve started to rise, to epoch 10. The maximum recorded mean flow and the area under the curve during epoch 11 were also analyzed.

Table 1 summarizes these results. It indicates that the increase in flow in response to acetylcholine was higher post treatment, since the maximum flow, the AUC during the increase and the AUC in epoch 11 were higher post treatment, to a statistically significant extent, even on the basis of four patients (the P value being 0.012, 0.020 and 0.040 respectively). The slope was also greater, but not significantly so.

TABLE 1

SUMMARY OF ANALYSIS OF IONTOPHORESIS DATA

| Drug | Variable | Baseline Before Treatment | | Visit 12 After Course of Treatment | | Visit 12 Minus Baseline | 95% Confidence Interval | P Value from T-Test |
| --- | --- | --- | --- | --- | --- | --- | --- | --- |
| | | Mean | SD | Mean | SD | | | |
| Acetyl Choline | Slope of Increase | 36.55 | 17.360 | 48.1 | 12.065 | 12.26 | −1.56, 26.08 | 0.067 |
| Acetyl Choline | Maximum Flow | 211.4 | 40.67 | 272.3 | 22.68 | 60.93 | 25.96, 95.89 | 0.012 |
| Acetyl Choline | AUC during increase | 80695 | 24238.1 | 106708 | 15247.0 | 26013 | 7899, 44127 | 0.020 |
| Acetyl Choline | AUC in epoch 11 | 64139 | 13167.0 | 83765 | 6622.3 | 19626 | 2106, 37145 | 0.040 |

EXAMPLE 5

Nineteen normal, healthy volunteers, 15 males, 4 females, aged between 20 and 30 years, were enrolled in the study. They were blindly assigned to two groups, 14 (10 males, 4 females) being given the treatment, the remaining 5 males constituting the control group. The volunteers were required to refrain from smoking during the study and to avoid taking drugs likely to affect platelet function, as recommended by the British Society of Haematology (1988). Individuals were bled by venepuncture, and re-injected with 10 mL of their own blood on five occasions over a period of two weeks. Thus the injections were administered at 2–3 day intervals according to the following protocol:

| Day | Bleed vol (ml) | Re-inject vol (ml) |
| --- | --- | --- |
| Mon | 40 | 10 |
| Wed | 20 | 10 |
| Fri | 20 | 10 |
| Mon | 20 | 10 |
| Wed | 10 | 10 |
| Wed(+2 h) | 30 | — |
| Fri | 10 | — |

Individuals in the treatment group received five intramuscular (gluteal) injections of 10 mL autologous blood which had been treated as described in Example 1 above. Individuals assigned to the control group were re-injected with 10 mL of their own untreated blood and the study was performed blind, in that neither the subjects, the supervising clinician nor the laboratory staff performing the analyses were aware of the group to which an individual was assigned.

Prostacyclin levels in peripheral blood were estimated from the plasma concentration of its stable metabolite, 6-keto-prostaglandin-F1α (Wu et.al., "Journal of Clinical Investigation" 75; 168–174, 1985), using a commercially available radioimmunoassay from Amersham International, U.K. The leukocyte surface markers CD25 (the α-subunit of the IL-2 receptor), the MHC Class 2 antigen HLA-DR and the monocyte-specific Ber-Mac 3 were assessed in mononuclear cells (monoctyes, T-cells and B-cells), isolated by density gradient centrifugation, using immunocytochemical staining with commercially available monoclonal antibodies. Quantitation of CD25, HLA-DR and Ber-Mac 3 positive cells was performed microscopically, with manual counting, and numbers were expressed as a percentage of the leukocyte common antigen positive (CD45+) cells.

Statistical Analysis: Significance was determined using Student's t-test for paired data to compare the post-treatment times with pre-treatment values. Results from control and treated groups of individuals were also compared.

Prostacyclin—Measured as 6-keto-prostaglandin F1α

The results from the treated group and control groups are shown in Tables 2 and 3. Table 4 shows a summary of the statistical analysis of these data. One subject (number 3) was excluded from the date due to cigarette smoking.

Within the treated group, the post-treatment 6-keto-PGF1α concentrations were significantly ($p<0.05$) higher on two of the five post-treatment measurement occasions, post-1 and post-4, when compared with the pre-treatment baseline values. No such significant differences were observed in the placebo-treated control group.

TABLE 2

The concentrations of 6-keto-prostaglandin F1α [pg/mL] in peripheral blood from treated volunteers before and after treatment.

| Treated Subject No. | Pre-Treatment (Baseline) | Post-1 | Post-2 | Post-3 | Post-4 | Post-5 |
| --- | --- | --- | --- | --- | --- | --- |
| 1 | 55.3 | 68.4 | 58.2 | 59.8 | 101.8 | 51.4 |
| 2 | 16.3 | 12.9 | 14.2 | 17.2 | 24.0 | 25.0 |
| 4 | 16.8 | 34.0 | 17.3 | 51.0 | 49.0 | 60.0 |
| 5 | 17.2 | 44.4 | 30.8 | 25.8 | 20.0 | 37.0 |
| 6 | 53.8 | 56.6 | 72.0 | 44.7 | 88.5 | 68.8 |
| 7 | 23.4 | 34.7 | 31.8 | 15.3 | 24.5 | 54.6 |
| 8 | 30.7 | 27.7 | 23.6 | 38.4 | 34.6 | 26.4 |
| 9 | 44.1 | 33.0 | 38.6 | 29.7 | 12.3 | 21.9 |
| 10 | 16.1 | 25.5 | 20.0 | 29.4 | 22.1 | 15.1 |
| 11 | 10.3 | 13.2 | 17.4 | 13.1 | 37.5 | 11.2 |
| 12 | 43.0 | 82.8 | 42.7 | 107.0 | 68.2 | 56.2 |
| 13 | 22.2 | 24.1 | 33.0 | 15.9 | 10.6 | 23.5 |
| 14 | 14.8 | 17.7 | 18.4 | 27.2 | 47.6 | 36.7 |
| Mean = | 28.00 | 36.54 | 32.15 | 36.50 | 41.59 | 37.52 |

TABLE 3

The concentration of 6-keto-prostaglandin F1α [pg/mL] in peripheral blood from placebo-treated (control) volunteers before and after a course of injections of untreated blood.

| Control Subject No. | Pre-Treatment (Baseline) | Post-1 | Post-2 | Post-3 | Post-4 | Post-5 |
| --- | --- | --- | --- | --- | --- | --- |
| 1 | 34.0 | 29.0 | 45.0 | 31.0 | 12.0 | 11.0 |
| 2 | 32.0 | 36.0 | 12.0 | 35.5 | 37.5 | 30.5 |
| 3 | 52.5 | 62.5 | 25.3 | 18.0 | 49.0 | 37.0 |
| 4 | 29.0 | 28.5 | 57.0 | 38.0 | 44.0 | 29.5 |
| 5 | 25.5 | 96.0 | 25.2 | 39.0 | 33.0 | 23.0 |
| Mean = | 34.60 | 50.40 | 32.90 | 32.30 | 35.10 | 26.20 |

TABLE 4

Statistical analysis of the data of Tables 2 and 3.

| Treatment Time | Baseline | 1 | 2 | 3 | 4 | 5 |
| --- | --- | --- | --- | --- | --- | --- |
| Control Baseline vs Control | — | 0.3191 | 0.8742 | 0.8003 | 0.941 | 0.1426 |
| Significance | | ns | ns | ns | ns | ns |
| Treated Basline vs Treated | — | 0.0434 | 0.0648 | 0.1672 | 0.0444 | 0.0687 |
| Significance | | <0.05 | ns | ns | <0.05 | NS |
| Treated vs Control | 0.3253 | 0.3758 | 0.9385 | 0.6107 | 0.5359 | 0.1208 |
| Significance | ns | ns | ns | ns | ns | ns |

Expression of CD25 on Peripheral Blood Mononuclear Cells

The proportion of cells expressing CD25, measured as a percentage of all CD45+ mononuclear cells, is shown in Tables 5 and 6 below. Table 7 shows the statistical analysis of these data. The results show that, on each of the five occasions investigated during and after a course of treatment, a significantly higher proportion of peripheral blood mononuclear cells expressed CD25 compared to the pre-treatment values. There was no such increased level of expression of this marker in the placebo treated control group. In addition, at post-treatment times 2 and 3 the treated group showed a significantly higher expression of this marker than the control group.

TABLE 5

The proportion of cells expressing CD25, as a percentage of CD45+ cells, in peripheral blood from treated volunteers before and after a course of treatment.

| Treated Subject No. | Pre-Treatment (Baseline) | Post-1 | Post-2 | Post-3 | Post-4 | Post-5 |
|---|---|---|---|---|---|---|
| 1 | 31 | 43 | 51 | 45 | 45 | 55 |
| 2 | 12 | 75 | 39 | 21 | 57 | 74 |
| 3 | 29 | 69 | 72 | 27 | 100 | 45 |
| 4 | 12 | 22 | 32 | 99 | 12 | 10 |
| 5 | 50 | 96 | 89 | 87 | 85 | 71 |
| 6 | 40 | 42 | 46 | 58 | 43 | 45 |
| 7 | 51 | 50 | 50 | 64 | 47 | 58 |
| 8 | 47 | 51 | 41 | 46 | 36 | 38 |
| 9 | 48 | 45 | 46 | 76 | 45 | 52 |
| 10 | 50 | 53 | 77 | 63 | 56 | 82 |
| 11 | 17 | 26 | 34 | 55 | 58 | 30 |
| 12 | 34 | 32 | 58 | 40 | 31 | 40 |
| 13 | 40 | 42 | 60 | 72 | 56 | 88 |
| 14 | 47 | 48 | 48 | 53 | 57 | 71 |
| Mean = | 36.29 | 49.57 | 53.07 | 57.57 | 52.00 | 54.21 |

TABLE 6

The proportion of cells expression CD25 (as a percentage of CD45+ cells) in peripheral blood from placebo-treated (control) volunteers before and after a course of injections of untreated blood.

| Control Subject No. | Pre-Treatment (Baseline) | Post-1 | Post-2 | Post-3 | Post-4 | Post-5 |
|---|---|---|---|---|---|---|
| 1 | 47 | 42 | 25 | 32 | 46 | 35 |
| 2 | 48 | 32 | 52 | 28 | 18 | 32 |
| 3 | 25 | 39 | 35 | 30 | 21 | 34 |
| 4 | 22 | 73 | 31 | 17 | 45 | 57 |
| 5 | 60 | 49 | 46 | 44 | 40 | 34 |
| Mean = | 40.40 | 47.00 | 37.80 | 30.20 | 34.00 | 38.40 |

TABLE 7

Statistical analysis of the data in Tables 5 & 6.

| Treatment Time | Baseline | 1 | 2 | 3 | 4 | 5 |
|---|---|---|---|---|---|---|
| Control Baseline vs Control Significance | — | 0.6175 | 0.7093 | 0.088 | 0.5189 | 0.8629 |
|  |  | ns | ns | ns | ns | ns |
| Treated Basline vs Treated Significance | — | 0.0322 | 0.0012 | 0.0042 | 0.0273 | 0.0043 |
|  |  | <0.05 | <0.002 | <0.005 | <0.05 | <0.005 |
| Treated vs Control Significance | 0.6343 | 0.7772 | 0.0442 | 0.0018 | 0.0535 | 0.0515 |
|  | ns | ns | <0.05 | <0.002 | ns | ns |

Expression of HLA-DR on Peripheral Blood Mononuclear Cells

The proportion of cells expressing HMA-DR, measured as a percentage of all CD45+ mononuclear cells, is shown in Tables 8 & 9 and Table 10 shows a summary of the statistical analysis of these data. As observed with CD25, the expression of HLA-DR was significantly enhanced on each of the five occasions investigated during and after a course of VasoCare™ therapy. Within the treated group, all post-treatment values were significantly higher than the pre-treatment baseline. As for CD25, no significant changes were observed in the control group. Comparison of the treated with the placebo group showed that, at post-treatment times 2, 3, 4, and 5, the treated group showed significantly greater i-DR expression than the control group.

TABLE 8

The proportion of cells expressing HLA-DR (as a percentage of CD45+ cells) in peripheral blood from treated volunteers before and after a course of treatment.

| Treated Subject No. | Pre-Treatment (Baseline) | Post-1 | Post-2 | Post-3 | Post-4 | Post-5 |
|---|---|---|---|---|---|---|
| 1 | 39 | 37 | 48 | 36 | 40 | 47 |
| 2 | 15 | 37 | 33 | 35 | 54 | 82 |
| 3 | 49 | 61 | 52 | 52 | 96 | 49 |
| 4 | 8 | 32 | 31 | 39 | 14 | 17 |
| 5 | 26 | 57 | 76 | 92 | 30 | 62 |
| 6 | 41 | 50 | 63 | 61 | 54 | 54 |
| 7 | 46 | 53 | 73 | 56 | 54 | 62 |
| 8 | 39 | 37 | 48 | 36 | 40 | 47 |
| 9 | 41 | 44 | 45 | 70 | 55 | 65 |
| 10 | 28 | 21 | 52 | 37 | 28 | 60 |
| 11 | 34 | 34 | 45 | 54 | 50 | 49 |
| 12 | 48 | 44 | 71 | 35 | 53 | 75 |
| 13 | 25 | 42 | 35 | 75 | 54 | 91 |
| 14 | 45 | 48 | 52 | 59 | 61 | 60 |
| Mean = | 34.57 | 42.64 | 51.71 | 52.64 | 48.79 | 58.57 |

TABLE 9

The proportion of cells expressing HLA-DR (as a percentage of CD45+ cells) in peripheral blood from placebo-treated (control) volunteers before and after a course of injections of untreated blood.

| Control Subject No. | Pre-Treatment (Baseline) | Post-1 | Post-2 | Post-3 | Post-4 | Post-5 |
|---|---|---|---|---|---|---|
| 1 | 20 | 15 | 19 | 17 | 14 | 24 |
| 2 | 39 | 44 | 42 | 32 | 31 | 41 |
| 3 | 28 | 36 | 30 | 33 | 33 | 47 |
| 4 | 33 | 30 | 37 | 39 | 47 | 56 |
| 5 | 55 | 33 | 43 | 51 | 35 | 40 |
| Mean = | 35.00 | 31.60 | 34.20 | 34.40 | 32.00 | 41.60 |

TABLE 10

Statistical analysis of the data in Tables 8 & 9.

| Treatment Time | Baseline | 1 | 2 | 3 | 4 | 5 |
|---|---|---|---|---|---|---|
| Control Baseline vs Control Significance | — | 0.5518 | 0.7978 | 0.8276 | 0.6331 | 0.3849 |
|  |  | NS | NS | NS | NS | NS |
| Treated Basline vs Treated Significance | — | 0.0223 | 0.0002 | 0.0072 | 0.0029 | 0.0008 |
|  |  | <0.05 | <0.0005 | <0.01 | <0.005 | <0.001 |
| Treated vs Control Significance | 0.9516 | 0.0871 | 0.0139 | 0.0309 | 0.0429 | 0.0355 |
|  | NS | NS | <0.02 | <0.05 | <0.05 | <0.05 |

Expression of Ber-Mac 3 Peripheral Blood Mononuclear Cells

The proportion of cells expressing Ber-Mac 3, a monocyte-specific surface marker, measured as a percentage of all CD45 positive mononuclear cells is shown in Tables 13 & 14 and Table 15 shows a summary of the statistical analysis of these data. As observed with the other leucocyte surface markers, the expression of Ber-Mac 3 was significantly enhanced during the course of therapy. Within the treated group, post-therapy values were significantly higher than the pre-treatment baseline at times 1 & 2. As in the case of the other two markers investigated, no significant changes were observed in the control group. Comparisons of the treated with the placebo group showed only a single significant difference of Ber-Mac 3 expression, at time 2.

TABLE 11

The proportion of cells expressing Ber-Mac 3 (as a percentage of CD45+ cells) in peripheral blood from treated volunteers before and after a course of therapy.

| Treated Subject No. | Pre-Treatment (Baseline) | Post-1 | Post-2 | Post-3 | Post-4 | Post-5 |
|---|---|---|---|---|---|---|
| 1 | 41 | 37 | 52 | 25 | 34 | 47 |
| 2 | 19 | 31 | 37 | 32 | 34 | 18 |
| 3 | 39 | 39 | 44 | 46 | 61 | 47 |
| 4 | 39 | 42 | 55 | 60 | 33 | 65 |
| 5 | 19 | 40 | 47 | 34 | 37 | 16 |
| 6 | 46 | 49 | 52 | 35 | 38 | 25 |
| 7 | 30 | 30 | 35 | 34 | 37 | 46 |
| 8 | 38 | 36 | 45 | 34 | 45 | 44 |
| 9 | 38 | 42 | 37 | 40 | 32 | 40 |
| 10 | 30 | 28 | 47 | 38 | 27 | 34 |
| 11 | 34 | 58 | 35 | 44 | 44 | 40 |
| 12 | 37 | 48 | 47 | 32 | 56 | 70 |
| 13 | 29 | 38 | 58 | 69 | 32 | 47 |
| 14 | 33 | 29 | 28 | 35 | 35 | 26 |
| Mean = | 33.71 | 39.07 | 44.21 | 39.86 | 38.93 | 40.36 |

TABLE 12

The proportion of cells expressing Ber-Mac 3 (as a percentage of CD45+ cells) in peripheral blood from placebo-treated (control) volunteers before and after a course of injections of untreated blood.

| Control Subject No. | Pre-Treatment (Baseline) | Post-1 | Post-2 | Post-3 | Post-4 | Post-5 |
|---|---|---|---|---|---|---|
| 1 | 29 | 21 | 25 | 27 | 26 | 31 |
| 2 | 30 | 27 | 36 | 41 | 49 | 43 |
| 3 | 35 | 76 | 38 | 33 | 54 | 68 |
| 4 | 19 | 21 | 36 | 29 | 39 | 64 |
| 5 | 38 | 20 | 38 | 36 | 23 | 22 |
| Mean = | 30.20 | 33.00 | 34.60 | 33.20 | 38.20 | 45.60 |

TABLE 13

Statistical analysis of the data in Tables 11 and 12.

| Treatment Time | Baseline | 1 | 2 | 3 | 4 | 5 |
|---|---|---|---|---|---|---|
| Control Baseline vs Control | — | 0.7955 | 0.2839 | 0.3832 | 0.3286 | 0.2290 |
| Significance | | ns | ns | ns | ns | ns |
| Treatment Baseline vs Treated | — | 0.0427 | 0.0019 | 0.1255 | 0.0845 | 0.0915 |

TABLE 13-continued

Statistical analysis of the data in Tables 11 and 12.

| Treatment Time | Baseline | 1 | 2 | 3 | 4 | 5 |
|---|---|---|---|---|---|---|
| Significance | | $p < 0.05$ | $p < 0.002$ | ns | ns | ns |
| Treated vs Control | 0.3889 | 0.6122 | 0.0147 | 0.1186 | 0.9167 | 0.6160 |
| Significance | ns | ns | $p < 0.02$ | ns | ns | ns |

What is claimed is:

1. A process for stimulating leukocytes in a mammalian patient comprising:

(a) extracting an aliquot of blood from the patient;

(b) subjecting the extracted aliquot of blood simultaneously to an elevated temperature stressor from 37° C. to 55° C., ultraviolet radiation stressor at a C-band wavelength, and an oxidative environment stressor comprising ozone thereby stimulating leukocytes in the aliquot of blood; and (c) reinjecting the blood aliquot into the patient.

2. The process according to claim 1, wherein the oxidative environment stressor is a gaseous oxidizing agent comprising a mixture of medical grade oxygen and ozone.

3. The process according to claim 2, wherein the gaseous oxidizing mixture comprises medical grade oxygen and 1.0–100 μg ozone per mL of the gaseous oxidizing mixture, applied to the aliquot at a rate of from 0.01–2.0 liters/minute.

4. The process according to claim 2, wherein the gaseous oxidizing mixture comprises medical grade oxygen and from 5–50 μg ozone per mL of the gaseous oxidizing mixture, applied to the aliquot at a rate of from 0.05–5.0 liters/minute.

5. The process according to claim 2, wherein the gaseous oxidizing mixture comprises medical grade oxygen and 12.5 μg ozone per mL of the gaseous oxidizing mixture, applied to the aliquot at a rate of 0.06 liters/minute.

6. The process according to claim 1 wherein the ultraviolet radiation stressor comprises output from a UV lamp emitting at a C-band wavelength.

7. The process according to claim 1 wherein the aliquot is human blood, and has a volume of from 0.1–100 mLs.

8. The process according to claim 1, wherein the aliquot has been subjected to said stressors for a period of time of from 0.5–60 minutes.

9. The process according to claim 1, wherein the ultraviolet radiation stressor comprises output from a UV lamp emitting at a wavelength of 253.7 nm.

10. The process according to claim 1, wherein the aliquot is human blood, and has a volume of 5–15 mLs.

11. The process according to claim 1, wherein the aliquot is human blood, and has a volume of 10 mLs.

12. The process according to claim 1, wherein the aliquot has been subjected to said stressors for a period of time of from 2–5 minutes.

13. The process according to claim 1, wherein the aliquot has been subjected to said stressors for a period of time of 3 minutes.

* * * * *